(12) United States Patent
Cline et al.

(10) Patent No.: US 8,155,893 B2
(45) Date of Patent: Apr. 10, 2012

(54) ENERGY FLOW MEASUREMENT IN GAS PIPELINES

(75) Inventors: Richard L. Cline, Missouri City, TX (US); Xiang Liu, Phoenix, AZ (US); Gregory M. Sanger, Chico, CA (US); Charles E. Smith, Liguna Niguel, CA (US); Xin Zhou, Rancho Cucamonga, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 13/236,310

(22) Filed: Sep. 19, 2011

(65) Prior Publication Data

US 2012/0004861 A1    Jan. 5, 2012

Related U.S. Application Data

(62) Division of application No. 12/684,061, filed on Jan. 7, 2010, which is a division of application No. 11/945,985, filed on Nov. 27, 2007, now Pat. No. 7,653,497.

(60) Provisional application No. 60/930,449, filed on May 15, 2007.

(51) Int. Cl.
   *G01N 31/00*         (2006.01)
(52) U.S. Cl. ......................................................... 702/28

(58) Field of Classification Search ..................... 702/28
   See application file for complete search history.

(56) References Cited

U.S. PATENT DOCUMENTS

| 6,940,599 | B1 * | 9/2005 | Hovde ........................ 356/432 |
| 7,197,403 | B2 * | 3/2007 | Morrow et al. ................ 702/27 |
| 2002/0197708 | A1 * | 12/2002 | Bachur, Jr. ................ 435/287.5 |
| 2006/0119851 | A1 * | 6/2006 | Bounaix ...................... 356/437 |

* cited by examiner

*Primary Examiner* — Drew A Dunn
*Assistant Examiner* — Stephen Cherry
(74) *Attorney, Agent, or Firm* — Mintz, Levin, Cohn, Ferris, Glovsky and Popeo, P.C.

(57) ABSTRACT

Thermodynamic properties of a natural gas stream can be determined in real time utilizing modeling algorithms in conjunction with one or more sensors for quantifying physical and chemical properties of the natural gas. A first data signal produced by a first sensor can include intensity as a function of wavelength. At least one region in the wavelength range outside of a selected absorption transition can be fitted to a function to obtain a zero-absorption baseline, and a carbon dioxide concentration can be determined based on a line strength at the selected absorption transition corrected by the zero-absorption baseline. A total hydrocarbon concentration in the gas stream can be inferred based on a database of characteristic natural gas concentrations, and an algorithm can be implemented that determines an energy content of the gas stream. Related techniques, apparatus, systems, and articles are also described.

18 Claims, 7 Drawing Sheets

ENERGY FLOW MEASUREMENT IN GAS PIPELINES

RELATED APPLICATIONS

The present patent application is a divisional of U.S. patent application Ser. No. 12/684,061, filed on Jan. 7, 2010 and entitled "Energy Flow Measurement In Gas Pipelines," which is a divisional of U.S. patent application Ser. No. 11/945,985, now U.S. Pat. No. 7,653,497, which issued on Jan. 26, 2010 and which in turn claims priority to U.S. Provisional Application Ser. No. 60/930,449, filed on May 15, 2007 and entitled "BTU Measurement in Gas Pipelines." Each application listed in this paragraph is incorporated by reference herein in its entirety.

TECHNICAL FIELD

The subject matter described herein relates to measurement of energy content flow in gas pipelines.

BACKGROUND

Recent deregulation and subsequent open access to the natural gas pipeline industry has strongly encouraged or, in some cases, forced gas businesses toward greater reliance on local energy flow rate measurement. What was once a large, stable, and well-defined source of natural gas is now a composite of many small suppliers with greatly varying gas compositions or involved with gas blending operations. While natural gas still has many advantages and its usage is increasing, it is no longer the inexpensive source of energy that it once was. Under-billing at tariff transfer points can cause revenue losses while over-billing can require accounts receivable corrections that can result in sizable additional costs.

One currently available approach to energy flow measurement uses a gas chromatograph (GC) for composition assay in conjunction with a flow meter. Such measurements are generally cost effective only for large capacity supplies (typically in applications where the volume is on the order of 1 to 30 million scf/day). The capital and the high maintenance costs of GC-based analysis systems can prevent their use in many applications. GC analysis can also be limited to measurements of only clean dry natural gas free of liquids or other contaminants that can foul the GC column. Such conditions are generally not present in a natural gas pipeline. GC systems can also suffer from slow analysis and calculation rates, with a typical analysis cycle requiring four or more minutes of sampling and analysis time. Natural gas moving at a pipeline velocity of 25 ft/sec travels over a mile in four minutes. Thus, a calculation of energy content flow based on GC measurements will in some applications be representative of gas that is already a mile or farther down the pipeline. Operation and maintenance costs of operating GCs can also be quite large due to the required consumable carrier gases and the regular maintenance required to assure that the instrument will continue to provide accurate data.

Another alternative method for measuring the potential energy of natural gas in a pipeline is calorimetry. The flame calorimeter is used to measure the properties of gas reactions. The gases concerned are fed at a known, constant rate to a jet at which the reaction occurs. The reaction chamber and gas pipes are contained in a thermostatically controlled water bath to ensure constant temperature. The reaction is then started and the temperature rise measured after a known amount of gas has been fed into the reaction. Calibration of the calorimeter, either with a standard reaction or by electrical means, allows calculation of the enthalpy ($\Delta H$) of the reaction because the reaction is conducted at constant pressure. Flame calorimetry can be performed in near real time depending on the design of the device employed. However, if the heated mass has a large heat capacity, it will take longer to register a meaningful temperature shift which results in a delay. In addition, calorimeter design is very difficult, especially for processes involving very small energy changes, e.g., energy changes on top of a large background such as pipeline gas. Maintenance and calibration of these devices may also require considerable resources.

SUMMARY

In one implementation of the current subject matter, an apparatus includes a first spectroscopic sensor that measures absorption of carbon dioxide in a gas stream and produces a first data signal characterizing a carbon dioxide concentration in the gas stream; a second spectroscopic sensor that measures absorption of hydrocarbons in the gas stream and produces a second data signal characterizing a total hydrocarbon concentration in the gas stream; and one or more third sensors producing one or more third data signals characterizing a temperature, a pressure, and a velocity of sound in the gas stream. The first, second, and third data signals are received by a master processor that implements an algorithm that determines an energy content of the gas stream using as inputs the carbon dioxide concentration, the total hydrocarbon concentration, the temperature, the pressure, and the velocity of sound characterized in the first, second, and third data signals.

In a second interrelated implementation, a first data signal characterizing a carbon dioxide concentration in a gas stream is received from a first spectroscopic sensor; a second data signal characterizing a total hydrocarbon concentration in the gas stream is received from a second spectroscopic sensor; and one or more third data signals characterizing a temperature, a pressure, and a velocity of sound in a gas stream are received from one or more third sensors. An algorithm is implemented that determines an energy content of the gas stream using as inputs the temperature, pressure, velocity of sound, carbon dioxide concentration, and hydrocarbon concentration characterized in the first, second, and third data signals.

In a third interrelated implementation, an apparatus includes a first sensor producing a first data signal characterizing a carbon dioxide concentration in the gas stream. The first sensor includes a tunable diode laser absorption spectrometer that measures carbon dioxide absorption at an effective wavelength to determine a carbon dioxide concentration in the gas stream. A master processor receives the first data signal and measurements of pressure and temperature in the gas stream. The master processor implements an algorithm that determines an energy content of the gas stream using as inputs the measured temperature, pressure, and carbon dioxide concentration, the algorithm inferring a total hydrocarbon concentration in the gas stream based on a database of characteristic natural gas concentrations.

In optional variations, the master processor can determine the carbon dioxide concentration in the gas stream based on the first data signal, determine the total hydrocarbon concentration based on the second data signal, and calculate a total nitrogen and inert species concentration in the gas stream as the remainder when the carbon dioxide and total hydrocarbon concentrations are subtracted from 100%. An apparatus can also optionally include one or more connections configured to attach to a fitting on a gas pipeline to divert the sample gas stream from the gas pipeline to the first, second, and third sensors. The one or more third sensors can optionally include an ultrasonic meter. The first sensor can optionally include a tunable diode laser absorption spectrometer that measures carbon dioxide absorption at an effective wavelength to determine a carbon dioxide concentration in the gas stream. The effective wavelength can optionally be in a range of approximately 2003 to 2004 nm. The second data signal can optionally include an absorption measurement measured at a single wavelength or in a single wavelength scan of a tunable diode laser and wherein the master processor uses the absorption measurement to calculate the total hydrocarbon concentration in the gas stream. The second sensor can also or alternatively optionally include a laser absorption spectrometer operating at a hydrocarbon characterization wavelength at which a total absorbance for hydrocarbons having fewer than 10 carbon atoms over an absorption path length of at least 10 cm is within a range of approximately 0.01% and 10.0% and the standard deviation of absorbances for the hydrocarbons having fewer than 10 carbon atoms is less than approximately 11%. The hydrocarbon characterization wavelength can optionally one of 2275.82 nm, 2270.31 nm, 2268.32 nm, 2262.10 nm, 2261.30 nm, 2261.15 nm, 2260.99 nm, 2260.87 nm, 2260.84 nm, 2260.32 nm, 2260.04 nm, 1694.05 nm, and 1694.02 nm.

In other optional variations, the second sensor can include a tunable diode laser absorption spectrometer that measures methane absorption at a first effective wavelength to determine a methane concentration in the gas stream and a laser absorption spectrometer operating at a hydrocarbon characterization wavelength at which a total hydrocarbon absorbance for hydrocarbons having between 2 and 10 carbon atoms over an absorption path length of at least 10 cm is within a range of approximately 0.01 and 10.0. The standard deviation of absorbances for the hydrocarbons having between 2 and than 10 carbon atoms can optionally be less than approximately 20%, and a methane absorbance for a 90% mole fraction of methane can optionally be less than approximately 1% of the total hydrocarbon absorbance for a 10% mole fraction of all C2-C10 absorptions at the path length of 10 cm.

The second sensor can also or alternatively optionally include a laser absorption spectrometer operating at a hydrocarbon characterization wavelength at which a total hydrocarbon absorbance for hydrocarbons having between 2 and 10 carbon atoms over an absorption path length of at least 10 cm is within a range of approximately 0.01 and 10.0. The standard deviation of absorbances for the hydrocarbons having between 2 and than 10 carbon atoms can optionally be less than approximately 20%, and a methane absorbance for a 90% mole fraction of methane can optionally be less than approximately 1% of the total hydrocarbon absorbance for a 10% mole fraction of all C2-C10 absorptions at the path length of 10 cm. The hydrocarbon wavelength can optionally be one of 3081.95 nm, 3082.23 nm, 3082.29 nm, 3082.35 nm, 3082.40 nm, 3082.46 nm, 3082.52 nm, 3083.78 nm, 3083.84 nm, 3083.89 nm, 3084.52 nm, 3084.58 nm, 3084.64 nm, 3084.70 nm, 3084.75 nm, 3084.81 nm, 3084.87 nm, 3084.93 nm, 3085.10 nm, 3085.15 nm, 3085.21 nm, 3087.16 nm, 3087.22 nm, 3087.28 nm, 3087.34 nm, 6718.02 nm, 6718.83 nm, 6731.37 nm, 6731.64 nm, and 6731.92 nm.

Computer program products, which may be embodied on computer readable-material, are also described. Such computer program products may include executable instructions that cause a computer system to conduct one or more of the method acts described herein. Similarly, computer systems are also described that may include a processor and a memory coupled to the processor. The memory may encode one or more programs that cause the processor to perform one or more of the method acts described herein.

Among other possible advantages, the subject matter described herein may be used to reduce capital and "operating and maintenance" (O&M) costs of natural gas energy content measurements in pipelines while also improving reliability, speed and accuracy. Energy producers and users may benefit from tighter gas inventory control, more efficient pipeline and industrial plant operations, and ultimately lower costs to the consumer. Suppliers have a need to monitor their product to assure that they are providing accurate measures of energy and consumers need to verify that their suppliers are giving correct measures.

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

This disclosure may be better understood upon reading the detailed description and by reference to the attached drawings, in which.

Like reference symbols may refer to like elements.

DETAILED DESCRIPTION

Figure 1:
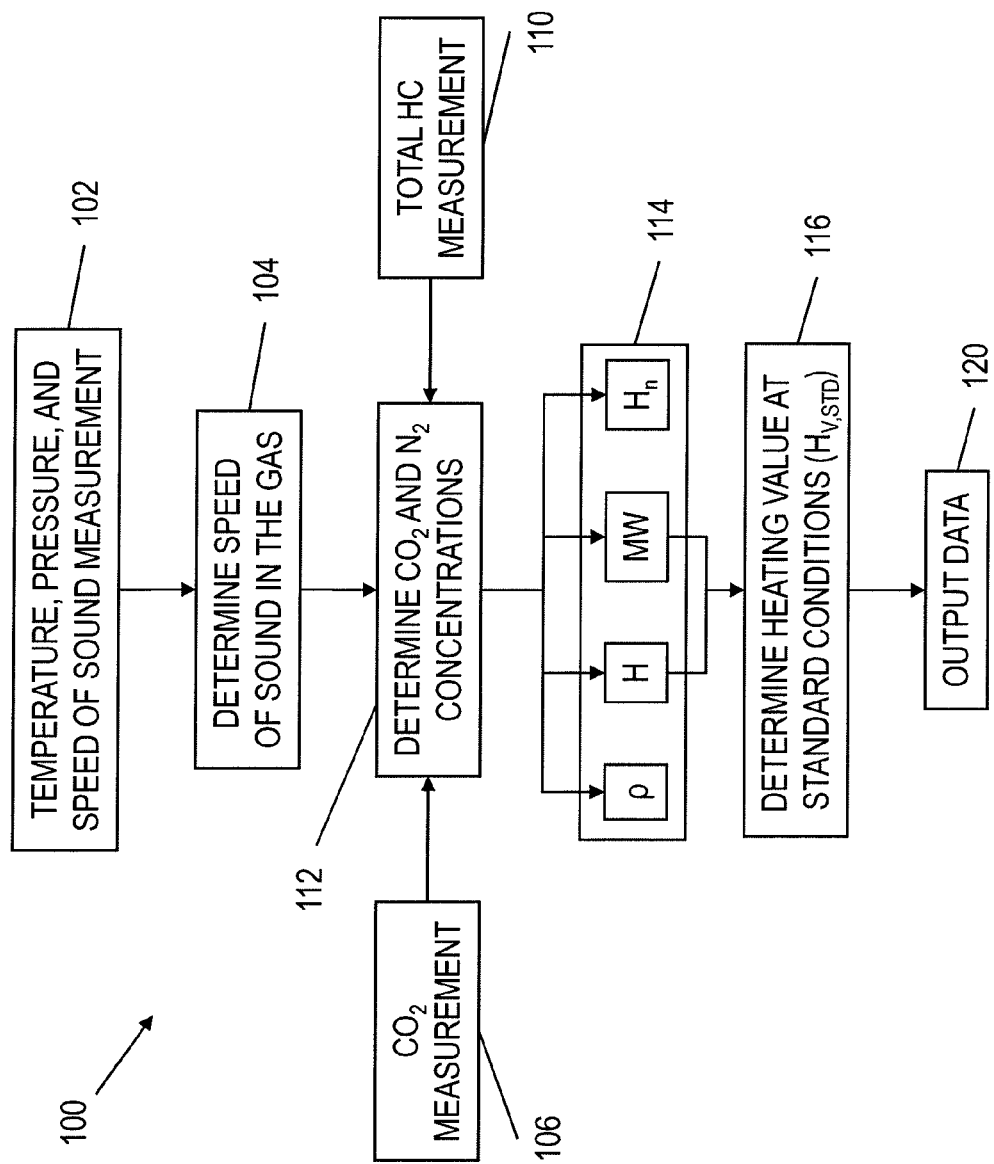
FIG. 1 is a process flow diagram showing a method of measuring the energy content of a gas stream.

The disclosed subject matter includes methods, techniques, systems, structures, and articles of manufacture that may be used to determine thermodynamic properties of a natural gas stream in real time using modeling algorithms and one or more sensors that measure physical and chemical properties of the natural gas stream. Such devices and systems can produce and process all information about the gas stream necessary to obtain a measurement of the energy content of the gas in real time without depending on database representations of standard stream constituent mixtures. To determine a sufficient set of natural gas characteristics to compute the energy content of the gas algorithmically, the velocity of sound in the gas is generally needed along with gas temperature and gas pressure, and one or the other of $CO_2+N_2$ or $CO_2$+total HC (from which the $N_2$ content can be inferred).

The energy content of natural gas can be determined by inference from measurements of directly measurable parameters. Such techniques have advantages in that they might be capable of providing energy content data sufficient to meet the monitor and transfer needs without the cost and other difficulties associated with GC measurements. An algorithmic inference method for estimating natural gas energy content generally relies on data correlations that relate energy measurement properties, such as for example molecular weight, mass-based heating value, standard density, molar ideal gross heating value, standard volumetric heating value, density, volume-based heating value, and the like, to inferential properties such as velocity of sound, carbon dioxide concentration, and nitrogen concentration. Temperature and pressure of the gas can be measured and used to calculate the gas component concentrations on a mass per volume basis. Data correlations can be used in conjunction with the measured variables to convert existing flow meters, such as for example ultrasonic, orifice, turbine, rotary, Coriolis, diaphragm, and the like for use in on-line energy measurement. Example algorithms and devices for conducting such measurements can be found in one or more of U.S. Pat. Nos. 7,197,403, 6,850,847, 6,704,660, and 6,604,051, the contents of all of which are hereby fully incorporated by reference.

While direct determination of the $N_2$ content of gas stream might be desirable, $N_2$ lacks readily measurable IR absorption characteristics, so TDLAS measurements can be difficult. Other methods for detecting $N_2$ are available but may not be feasible for the natural gas industry due to the hazardous nature of the environment, complexity of the measurement system and the associated costs. Two potential approaches include converting $N_2$ into NO using a plasma burner and then determining the concentration of NO using chemiluminescence and using flame ionization detection or plasma emission detection. Both techniques are hazardous and expensive in the natural gas distribution industry.

In addition to nitrogen and carbon dioxide, natural gas also typically includes methane ($C_2H_4$), ethane ($C_2H_6$), propane ($C_3H_8$), iso-butane ($iC_4$) and n-butane ($nC_4$), iso-pentane ($iC_5$) and n-pentane ($nC_5$), n-hexane ($nC_6$), n-heptane ($nC_7$), n-octane ($nC_8$), n-nonane ($nC_9$), n-decane ($nC_{10}$), hydrogen (H2), hydrogen sulfide ($H_2S$), oxygen ($O_2$), water ($H_2O$), carbon monoxide (CO), helium (He), and argon (Ar). In most natural gas streams, $O_2$, $H_2O$, CO, He, Ar, and $H_2S$ are only found in trace amounts and do not have any significant affect on the stream's energy properties. Therefore, they can typically be ignored in these types of measurements. Additional parameters necessary to fully and accurately characterize the energy content of a natural gas mixture having a variable composition include the speed of sound in the gas; temperature and pressure of the gas; and concentrations of components of the gas such as $CO_2$, $N_2$, and the total number of hydrocarbons from $C_2$ to $C_{10}$. Measurement of the speed of sound, the temperature, and the pressure can be made directly by velocity of sound sensors. The $CO_2$ concentration can be measured using a spectroscopic technique, such as IR Tunable Diode Laser Absorption Spectroscopy (TDLAS). Similarly, a spectroscopic technique such as IR laser absorption spectroscopy can be used to measure the total hydrocarbon content of the natural gas stream. With a measurement of the total hydrocarbon content of the gas and all other significant gas components, it is possible to determine the $N_2$, the only remaining gas present, by subtraction. With all necessary measurements available in real time, additional calculations can be made to estimate the molecular weight of the subject gas, which can then be used as the basis for mass flow calculations, to determine the speed of sound at standard pressure and temperature, and finally, the various thermo-physical characteristics of the gas including its heating value.

An algorithmic technique can be used to characterize the thermo-physical properties of natural gas hydrocarbon mixtures with a single inferential property when the concentrations of the diluent gases (carbon dioxide and nitrogen) are known. The single inferential property can be the speed of sound in the natural gas mixture as determined at a known pressure and temperature. The speed of sound forms the necessary input to the algorithms developed for the purpose of thermo-physical property computation. An instrument can use such an algorithm in concert with direct or indirect measurements of the necessary gas properties (temperature, pressure, and density) and diluent concentrations (e.g., nitrogen and carbon dioxide) of hydrocarbon gas streams. The system then computes values for the thermo-physical properties of such streams directly and without reliance on external databases. The energy flow, heating value and other related thermo-physical properties are determined using such an algorithm.

In some implementations of the current subject matter, gas concentrations are measured or inferred from other direct measurements to calculate energy content values that are sufficiently accurate to be practical for the measurement and tariff transfer purposes in the natural gas distribution industry. The concentration of the total of the hydrocarbon components of the gas (the majority of the gas mixture) can be determined by a single simultaneous measurement of the entire $C_1$-$C_{10}$ group of gases by TDLAS spectroscopy. This measurement can be used to determine the amount of $N_2$ present in the stream, without differentiating the carbon-containing species.

FIG. 1 is a process flow diagram 100 showing a method of determining the energy content of a gas stream. Measurements of pressure, temperature, and the velocity of sound in a gas stream are conducted at 102. These measurements can be made with an ultrasonic meter or other comparable device that can be used to determine, compute, or measure the density of a gas. The speed of sound in the gas is determined at 104 based on the measurements and fed as one input to a processor that also receives measurements of carbon dioxide at 106 and total hydrocarbons at 110. The carbon dioxide measurement at 106 and/or the total hydrocarbon measurement at 110 can be accomplished using a spectrometer as described in greater detail below. The three inputs are used to determine a carbon dioxide and a nitrogen concentration in the gas stream at 112 based on an algorithm described in greater detail below. The algorithm calculates gas density ($\rho$), heating value (H), effective molecular weight (MW), and ideal gross heating value ($H_n$) at 114. These calculated values can be used to determine the gas heating value at standard conditions at 116. At 120, one or more of the measured and/or calculated values can be output to an external device, such as a display, a computer, a database, a hard copy, or the like.

Figure 2:
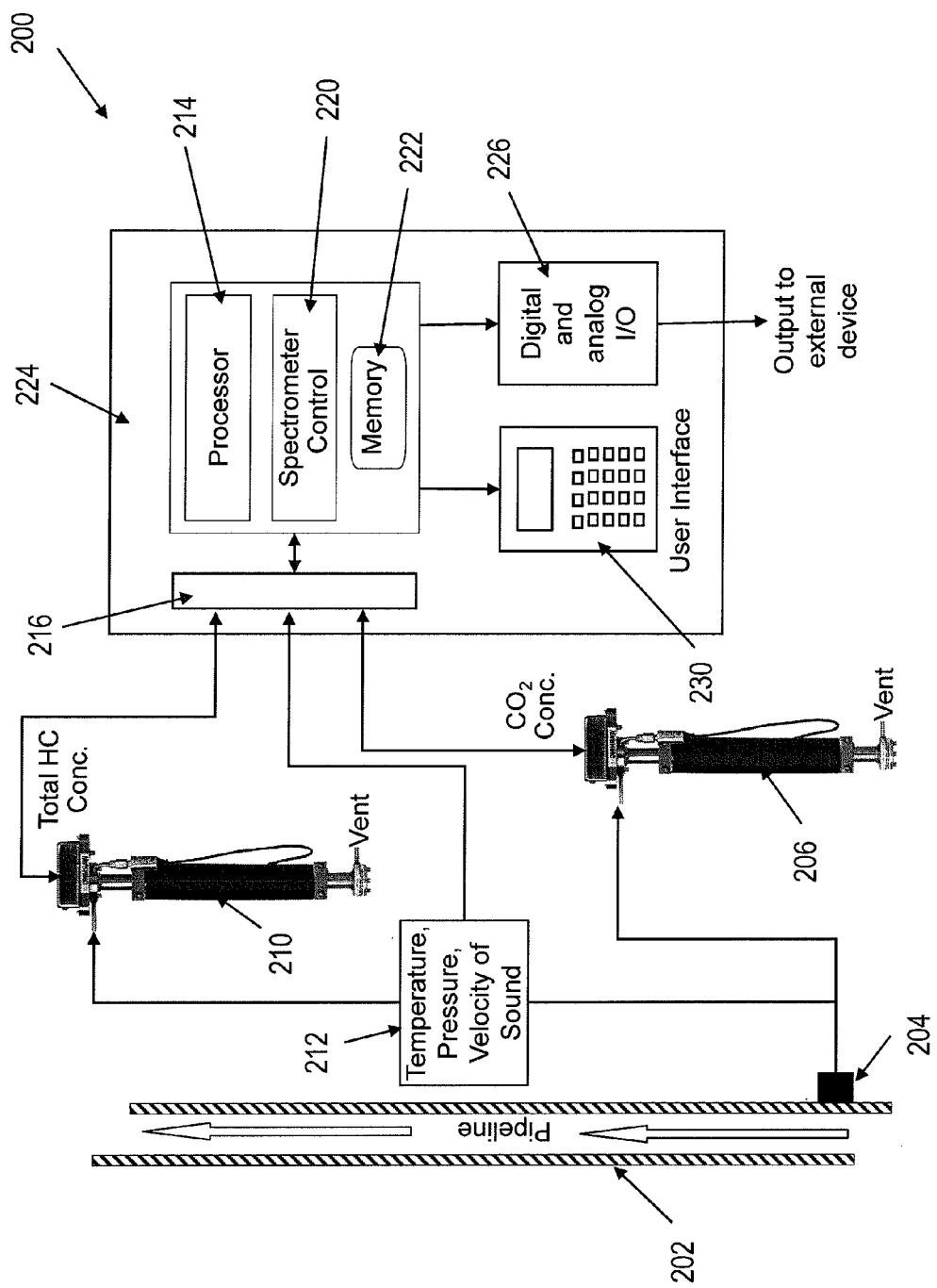
FIG. 2 is a diagram showing components of an energy meter.

Another implementation of the current subject matter is shown in FIG. 2. Gas from a pipeline 202 or other source of natural gas or similar gas whose heating value is of interest can be diverted to a sensor system via an inlet tap 204 or other comparable device. Gas removed from the pipeline 202 can flow through a first sensor 206, a second sensor 210, and a third sensor 212. The first sensor 206 can be a spectroscopic sensor system configured to quantify carbon dioxide in the gas stream, and the second sensor 210 can be a second spectroscopic sensor configured to quantify total hydrocarbons in the gas stream. Both the first sensor 206 and the second sensor 210 can be laser absorption spectrometers. The third sensor 212 can be an ultrasonic meter or other device for determining the temperature and pressure of, and the velocity of sound in the diverted gas stream. The third sensor 212 need not be a single device that calculates all three values, but can be a combination of one or more sensors that provide the desired measurements.

A processor 214 can receive data signals from the first, second, and third sensors, optionally via a data interface 216, such as for example a analog to digital converter. The processor 214 can be associated with spectrometer control electronics 220 and a system memory 222 which can store the calculation algorithm and/or one or more processor routines as well as software for operating the first, second and third sensors. The spectrometer control electronics 220, which can control the first 206 and the second 210 sensors, can be implemented on one or more second processors or can alternatively be integrated with the processor 214. The processor 214, spectrometer control electronics 220, memory 222, data interface 216, and the like can be contained within a processor enclosure 224. A digital and/or analog input/output device 226 for passing data to one or more external devices and for receiving input commands for the sensor system can be included, as can a user interface 230. The algorithm can in one example by the MPX algorithm developed by Integrated Information Technologies, Inc. (now SpectraSensors, Inc. of Rancho Cucamonga, Calif.). The sensor system can also include means for sample conditioning and pipeline extraction to facilitate installation in natural gas pipeline situations.

IR absorption spectrometers can be used to measure concentrations of gases as to the measurement of gas concentrations in combination with the measurement of pressure, temperature and velocity of sound (VOS) from the USM. The first sensor 206 for measuring $CO_2$ can optionally be a TDLAS spectrometer. The length of the path in the first sensor 206 can be selected based on the strength of the absorption line being employed. In general, the stronger the absorbance, the shorter the path. For short paths, the light source (a tunable diode laser) and the detector can be placed at opposite ends of the absorption path. When the path needs to be longer the laser and the detector can be located at the same end of the path with a mirror at the opposite end. In this manner, the light traverses the "cell" length twice. When even longer cell are required, a Herriott cell, that allows the light to traverse between two concave spherical mirrors many times, can be employed. Herriott cells with path lengths of 100 M or greater can be employed in these types of measurements. Other types of optical cells that employ more complex technology can have effective path lengths of several thousand meters by causing a path length between the light source and the photodetector to traverse a sampled volume of gas many times.

For $CO_2$ and the wavelengths in the range of 1300 to 2100 nm, a harmonic spectroscopy technique can be employed in connection with its TDL light source to greatly improve the signal to noise of the spectrometer. The TDL laser light source wavelength can be modulated at a high frequency (kHz-MHz) and the detection of the signal can be performed at a multiple of the modulation frequency. If the detection is performed at twice the modulation frequency, the term second harmonic or "2f" spectroscopy is used. Advantages to this technique include the minimization of 1/f noise, and the removal of the sloping baseline that can be present on TDL spectra (due to the fact that the laser output power increases as the laser injection current increases, and changing the laser injection current is how the laser is tuned).

A combination of a slow ramp and a fast sinusoidal modulation of the wavelength can be used to drive the diode laser. The photodetector in the spectrometer can receive this modulated intensity signal. The $n^{th}$ harmonic component can be resolved by demodulating the received signal. Detection using the signal at the second harmonic (2f) can be used. The 2f lineshape is nearly symmetric and peaks at line center due to the nature of even function. Additionally, the second harmonic (2f) provides the strongest signal of the even-numbered harmonics. By shifting detection to higher frequency, 2f spectroscopy can significantly reduce 1/f noise and thus provide a substantial sensitivity enhancement compared to direct absorption methods.

In another implementation, direct absorption spectroscopy can be used to quantify carbon dioxide. In this implementation, the frequency of the laser source in the spectrometer can be tuned over the selected absorption transition and the zero-absorption baseline can be obtained by fitting the regions outside the absorption line to a low-order polynomial. The integrated absorbance is directly proportional to the concentrations of absorbing species in the laser path length as well as the line strength of the transition.

The choice of photodetectors used in the first sensor can depend on the specific wavelengths of the lasers and absorption lines to be measured. One possible photodetector is an indium gallium arsenide (InGaAs) photodiode sensitive to light in the 1200 to 2600 nm wavelength region. For longer wavelengths, an indium arsenide photodiode, sensitive for wavelengths up to approximately 3.6 μm, can be used. Alternatively, indium antimonide detectors are currently available for wavelengths as long as approximately 5.5 μM. Both of the indium devices operate in a photovoltaic mode and do not require a bias current for operation. These photodetectors, which lack low frequency noise, are advantageous for DC or low frequency applications. Such detectors are also advantageous for high speed pulse laser detection, making them particularly useful in trace gas absorption spectroscopy. Other photodetectors, such as for example indium arsenide (InAs), silicon (Si), or germanium (Ge) photodiodes and mercury-cadmium-telluride (MCT) and lead-sulfide (PbS) detectors, may also be used.

The signal from the first sensor 206 can be developed and recorded by the processor 214 four times per second or at some other acceptable interval. The processor 214 can determine the concentration of carbon dioxide in the gas stream by computing the absorbance of the gas as a ratio between the zero and the measured value of absorbance at the peak of the absorbance line. This absorbance is a function of the gas pressure and temperature in the cell so the absorbance is adjusted by a pressure/temperature calibration matrix stored in the microprocessor memory. This matrix can be developed on an analyzer-by-analyzer basis.

Once the corrected absorbance value is determined, the concentration can be computed from the Beer-Lambert law, which states that the amount of light at a specific wavelength transmitted through a known length of optical path containing a target gas is proportional to the concentration of the gas species that absorbs at that wavelength of light:

$$C = A/\epsilon L \qquad (1)$$

where C is the concentration, A is the absorption, $\epsilon$ is the extinction coefficient for the gas of interest and L is the path length of the absorption/sample cell. This concentration can be converted into ppmv, lbs/mmscf averaged and sent to the outputs once per second.

As noted above, the second sensor 210 can provide a measurement of the total hydrocarbon content in the natural gas stream using spectroscopic techniques. The total hydrocarbon concentration, in conjunction with the known carbon dioxide concentration, can then be used to determine the nitrogen concentration by difference. Given the concentrations of hydrocarbons and carbon dioxide, it can be assumed in some implementations that the remainder of the gas composition is nitrogen or other similarly inert gas species. The nitrogen concentration is the fifth gas characteristic used to determine the thermo-physical properties of the gas.

In one implementation, a fixed-wavelength TDL or NDIR approach can optionally be used to measure the mole fraction of total hydrocarbons in the gas stream. This technique can make use of two channels: one fixed at a selected wavelength to measure the total absorbance of the HCs and the other providing a zero-absorption baseline/reference. The baseline or reference signal can be obtained in one of a number of possible ways. In one variation, the necessary spectroscopic data can be obtained by switching the gas introduced into the absorption cell of the third sensor at regular intervals (switching interval is adjustable depending on the stability of the background gas). The sample cell can be flushed with an inert gas such as $N_2$ or air and the transmission signal with the same laser and detector giving the background absorbance. Switching it back to the pipeline gas mixture will allow the difference to be obtained amounting to a measure of the total HC concentration.

In another variation, two laser beams can be multiplexed. One of the laser beams can be a non-resonant laser beam (running at a wavelength where all the HC's have negligible absorptions) that provides a background measurement. This laser uses the same path or cell as the laser that is making the HC concentration determination. The advantage of using a non-resonant laser wavelength is that it is able to account for the non-absorbing transmission loss. This can be a more costly solution because it requires two lasers, at least one wavelength beam splitting element (a grating, polarizing beam splitter or thin film beam splitter) and two separate detectors. It is possible to accomplish a similar effect using temporal multiplexing techniques which eliminate some of the expense. However, two lasers are still generally used unless the resonant and non-resonant wavelengths are close enough to be covered by one laser, along with one detector.

In yet another variation, a ratiometric technique can be employed in which a single wavelength laser beam is split into two parts. One part of the laser beam is passed through a measurement path or cell and the second through another identical path or cell with inert gas or directly to detector. While this is an improvement to the two laser, two detector solution, it is unable to completely account for the non-absorbing transmission loss along the main sample cell.

Figure 3:
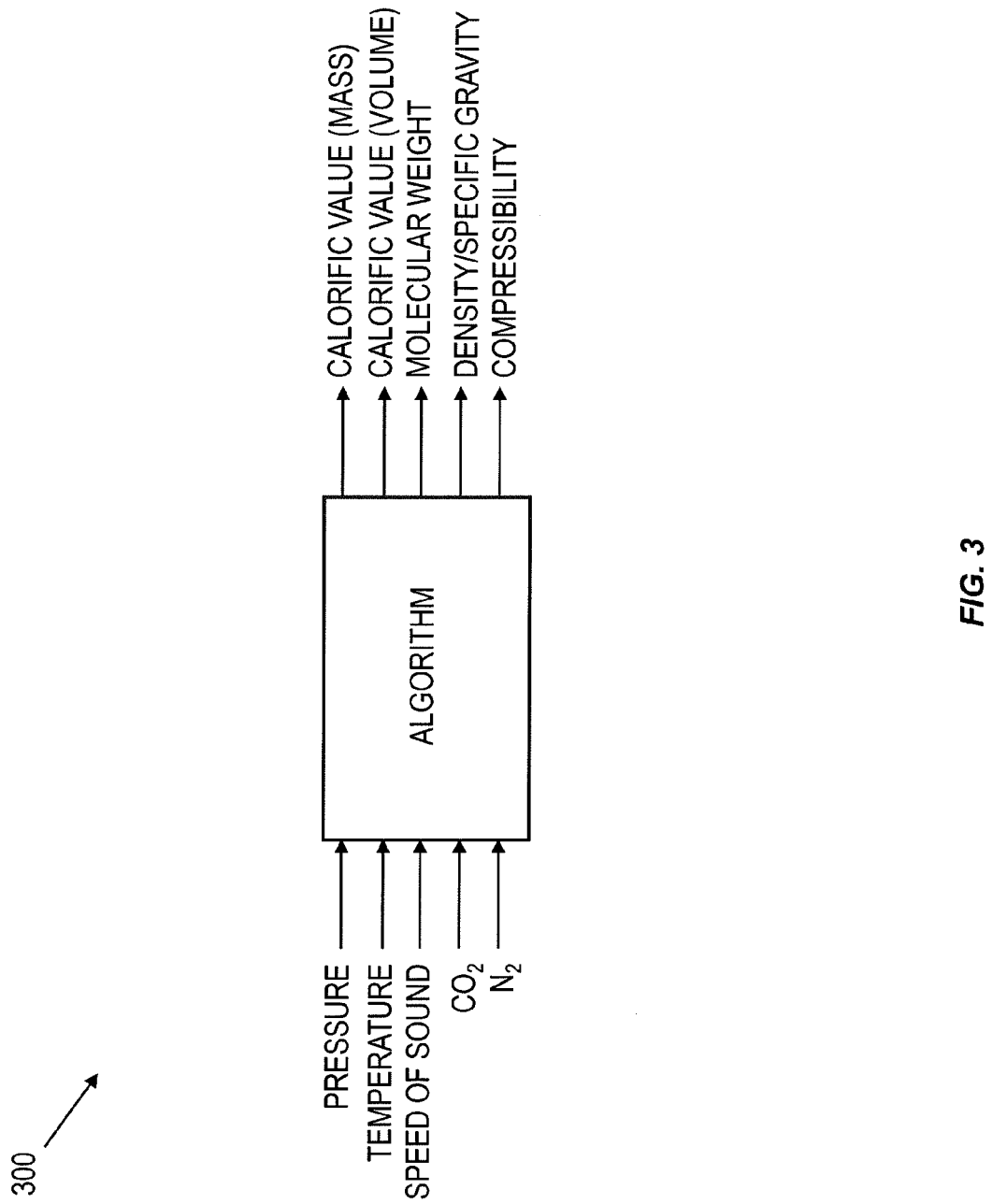
FIG. 3 is a diagram illustrating operation of an algorithm for determining the energy content of a gas stream.

FIG. 3 shows a flow diagram 300 of an algorithm for inferential computational measurement of energy flow in a natural gas pipeline. As indicated above, the known parameters, including pressure, temperature, and the speed of sound, as well as concentrations of the dilute components of pipeline gas are inputs to the algorithm. Using the speed of sound with known pressure, temperature, $CO_2$, and $N_2$ concentrations, the density of the subject gas can be determined. Additional calculations, such as for example using the density and a set of reference gases, can be performed to determine the thermo-physical characteristics of the gas.

Flow of natural gas can be measured as a volumetric flow rate (for example by an ultrasonic meter, turbine meter, rotary meter, diaphragm meter, or the like), on a differential basis (for example with an orifice meter, and annular meter, a V-cone meter, or the like) or as a mass flow rate (for example using a Coriolis meter, thermal-mass meter, or the like). For a volumetric flow rate at a given temperature, $Q_v$, the energy content flow rate, $Q_{energy}$, is given by $$Q_{energy} = Q_{v,std} \cdot H_{v,std} \quad (2)$$
$$= \left(\frac{\rho \cdot Q_v}{\rho_{std}}\right)(\rho_{std} \cdot H_m)$$
$$= Q_v(\rho \cdot H_m)$$
$$= Q_v \cdot H_v$$

where $H_v$ is the volumetric energy content (energy per volume), $\rho$ is the gas density, $H_m$ is the mass-based energy content (energy per mass), and the subscript std denotes values determined at standard conditions of 60° F. (15.5° C.) and 14.696 psia (0.1013 MPa).

For differential flow meters, which are based on pressure measurements, $Q_{energy}$, is given by $$Q_{energy} = Q_{v,std} \cdot H_{v,std} \quad (3)$$
$$= \left(\frac{C \cdot \sqrt{\rho}}{\rho_{std}}\right)(\rho_{std} \cdot H_m)$$
$$= C(\sqrt{\rho} \cdot H_m)$$

where C is a correction factor that depends on the gas viscosity and the isentropic exponent. The energy content flow for mass-based measurements is given by $$Q_{energy} = Q_{v,std} \cdot H_{v,std} \quad (4)$$
$$= \left(\frac{Q_m}{\rho_{std}}\right)(\rho_{std} \cdot H_m)$$
$$= Q_m H_m$$

which depends only on the mass-based gas flow rate, $Q_m$, multiplied by the mass-based heating value, $H_m$.

As indicated by equations 2-4, three main values are needed to calculate the heating value for a sample of natural gas, two chemical properties: $H_m$, $\rho_{std}$, and one thermodynamic property: $\rho$. Other chemical values, such as the mixture molecular weight, MW (mass per mol), the mixture molar ideal gross heating value, $H_{n,ref}$ (energy per mol, with chemical enthalpies referenced to standard conditions). MW can be used as a data correlation intermediary to characterize gas composition and may also be used to calculate the ideal specific gravity of a gas mixture. $H_{n,ref}$ can be used as a data correlation intermediary to characterize gas composition, especially the gas density, $\rho$ from an existing equation of state.

$H_m$, $\rho_{std}$, MW, and $H_{n,ref}$ can be calculated for a gas mixture using the equations shown below, and the measured inputs of gas temperature, pressure, speed of sound, mole fraction of $CO_2$, and mole fraction of $N_2$, which can be determined using the total hydrocarbon concentration, as discussed above.

The real gas state equation can be used to define the standard density, $\rho_{std}$, as $$\rho_{std} = \frac{P_{std} \cdot MW}{Z \cdot R \cdot T_{std}} \quad (5)$$

where $P_{std}$ and $T_{std}$ are standard pressure and temperature in absolute units, Z is the compressibility factor, and R is the universal gas constant. Since $P_{std}$, $T_{std}$, and R are all constants, $\rho_{std}$ is a function of only the variable ratio MW/Z. Then, algorithms can be employed to calculate the heating value or energy content of the gas. In one example, the algorithm as described in one or more of U.S. Pat. Nos. 7,197,403, 6,850,847, 6,704,660, and 6,604,051, the disclosures of which are incorporated herein by reference. The currently disclosed subject matter can be use din conjunction with such algorithms without the need for inferring the input values used in the algorithms. Instead, the input values are determined by direct measurement or, in the case of the nitrogen concentration, by mathematical derivation from one or more direct measurements.

Table 1 shows common natural gas pipeline gas components and the typical, although approximate, relative mole fractions of the various species. As can be seen, methane is the dominant HC component in natural gases (generally >80%). $C_1$-$C_4$ are usually found in the parts per hundred range while $C_{6+}$ is usually less than 1% as are iso-pentane and n-pentane.

TABLE 1

Typical Pipeline Gas Composition

| Component | Mole Fraction |
|---|---|
| Methane ($CH_4$) | 70-96% |
| Ethane ($C_2H_6$) | 0-20% |
| Propane ($C_3H_8$) | 0-20% |
| Butane ($C_4H_{10}$) | 0-20% |
| Pentane ($C_5$) | 0-0.14% |
| Hexanes+ ($C_6$+) | 0-0.04% |
| Carbon Dioxide ($CO_2$) | 0-8% |
| Oxygen ($O_2$) | 0-0.2% |
| Nitrogen ($N_2$) | 0-5% |
| Hydrogen ($H_2$) | 0-0.02% |
| Hydrogen Sulfide ($H_2S$) | 0-5% |
| T-Butyl Mercaptan ($C_4H_{10}S$) | 0-50 ppm |
| Methyl Ethyl Sulfide ($C_2H_6S$) | 0-5 ppm |
| Rare gases (A, He, Ne, Xe) | Trace |

Table 2 lists candidate wavelengths for use in determination of the total hydrocarbon concentration. The wavelengths in Table 2 have been selected based on $C_1$-$C_{10}$ hydrocarbons having similar levels of absorbance and the following two criteria being met: the total absorbance for all 12 HC's in an absorption cell of at least 10 cm in path length is within 0.01% and 10.0%, and the standard deviation of these 12 absorbances at a given wavelength is less than approximately 11%.

TABLE 2

Candidate Wavelengths for Total Hydrocarbon Measurement

| Frequency (cm$^{-1}$) | Wavelength (nm) | Total Absorbance | STD (%) |
|---|---|---|---|
| 4394.03 | 2275.82 | 0.42 | 10.6 |
| 4404.69 | 2270.31 | 0.42 | 9.0 |
| 4408.55 | 2268.32 | 0.43 | 10.0 |
| 4420.66 | 2262.10 | 0.35 | 10.8 |
| 4422.23 | 2261.30 | 0.33 | 10.4 |
| 4422.53 | 2261.15 | 0.33 | 9.4 |
| 4422.83 | 2260.99 | 0.32 | 10.5 |
| 4423.08 | 2260.87 | 0.32 | 10.7 |
| 4423.14 | 2260.84 | 0.31 | 10.6 |
| 4424.16 | 2260.32 | 0.30 | 11.0 |
| 4424.70 | 2260.04 | 0.29 | 10.7 |
| 5903.00 | 1694.05 | 0.17 | 10.9 |
| 5903.12 | 1694.02 | 0.16 | 11.7 |

Figure 4:
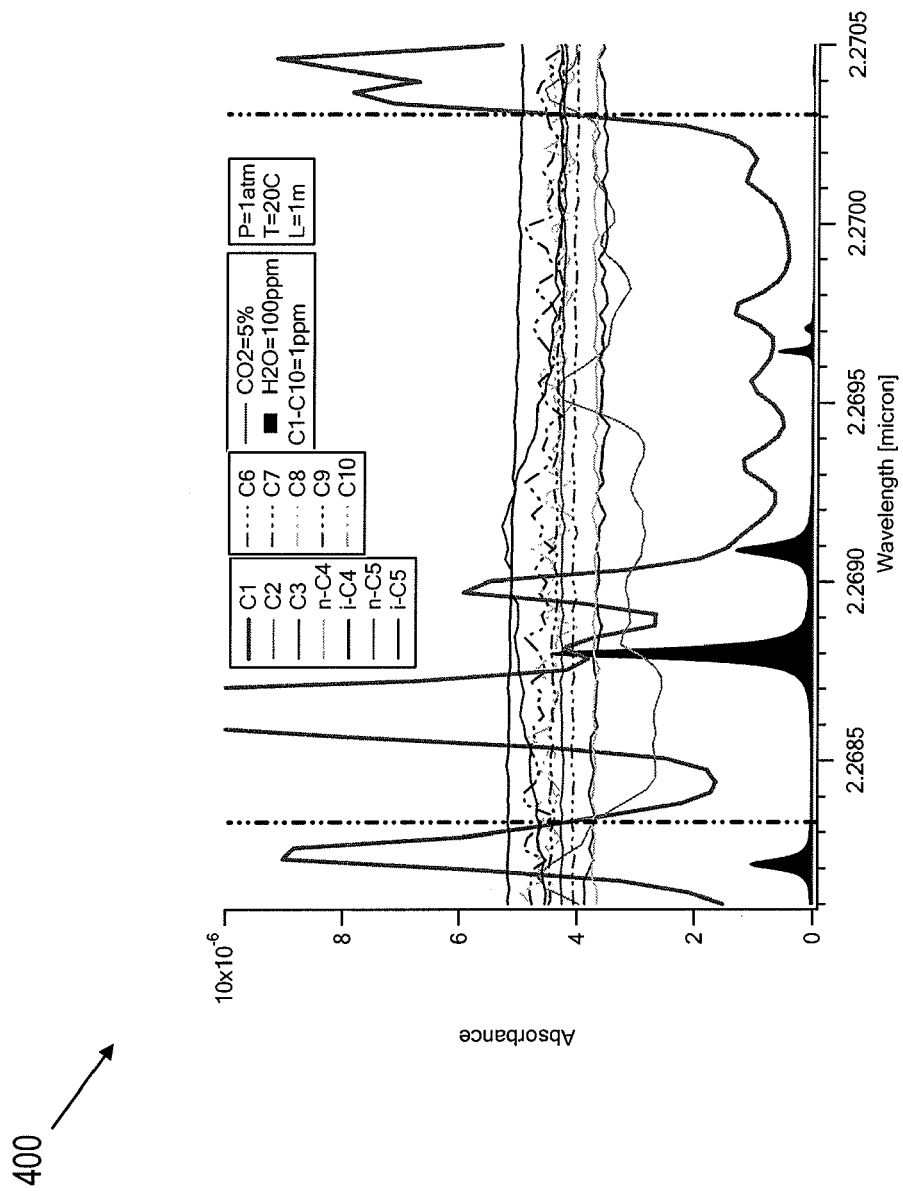
FIG. 4 is a graph showing absorption spectra for hydrocarbons having between one and ten carbons at wavelengths near 2.269 µm.
Figure 5:
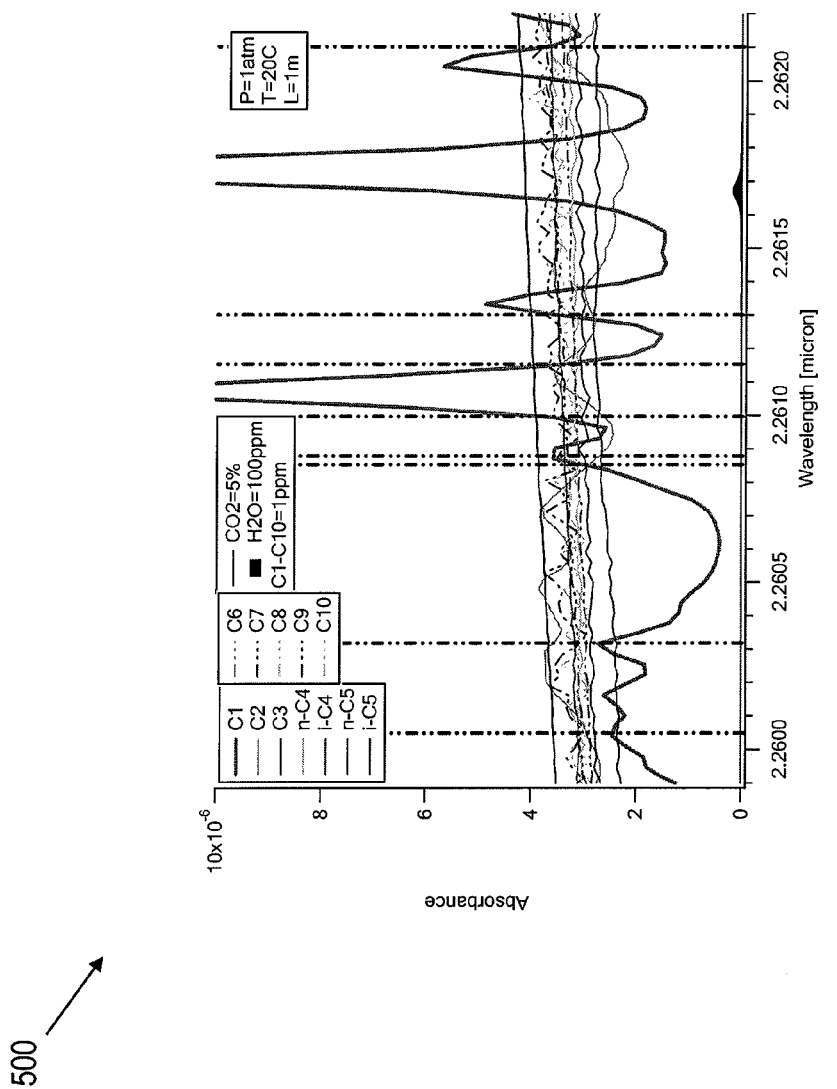
FIG. 5 is a graph showing absorption spectra for hydrocarbons having between one and ten carbons at wavelengths near 2.261 µm.
Figure 6:
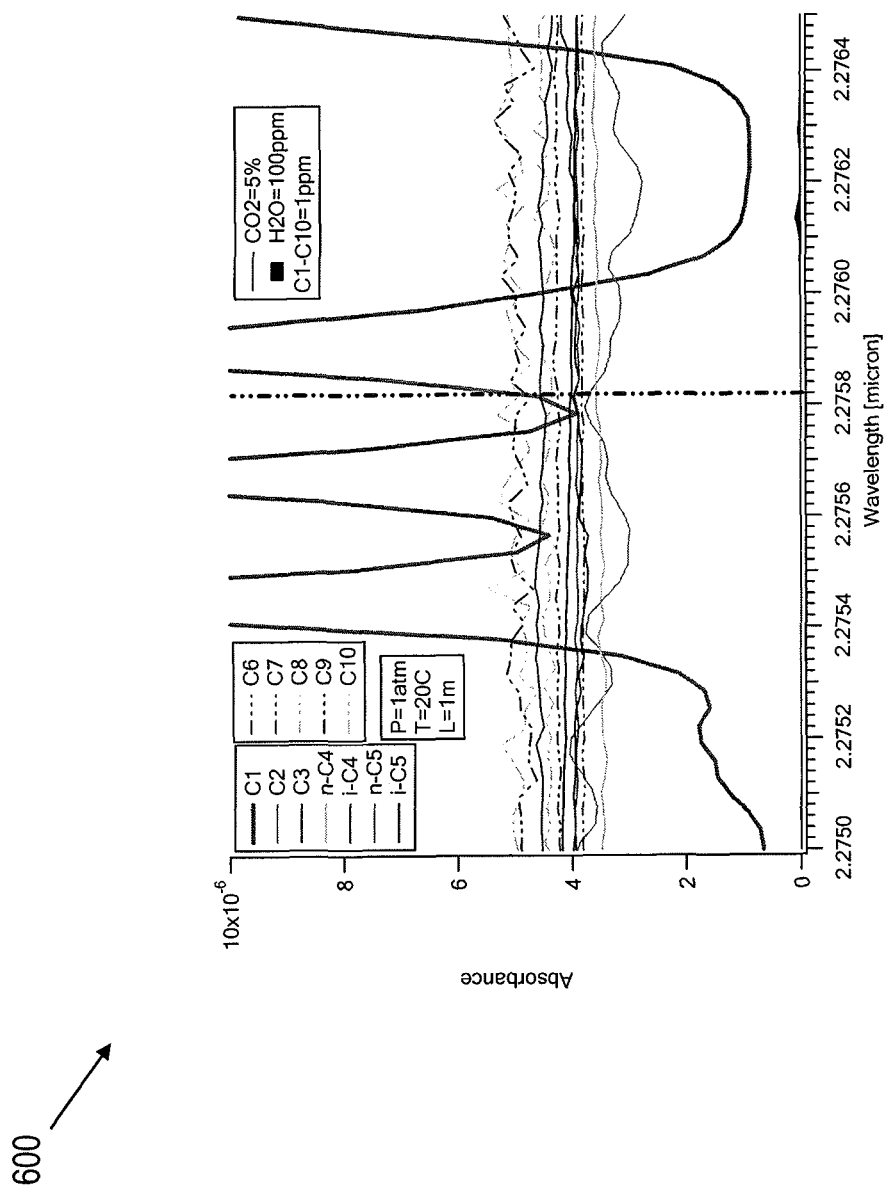
FIG. 6 is a graph showing absorption spectra for hydrocarbons having between one and ten carbons at wavelengths near 2.276 µm.
Figure 7:
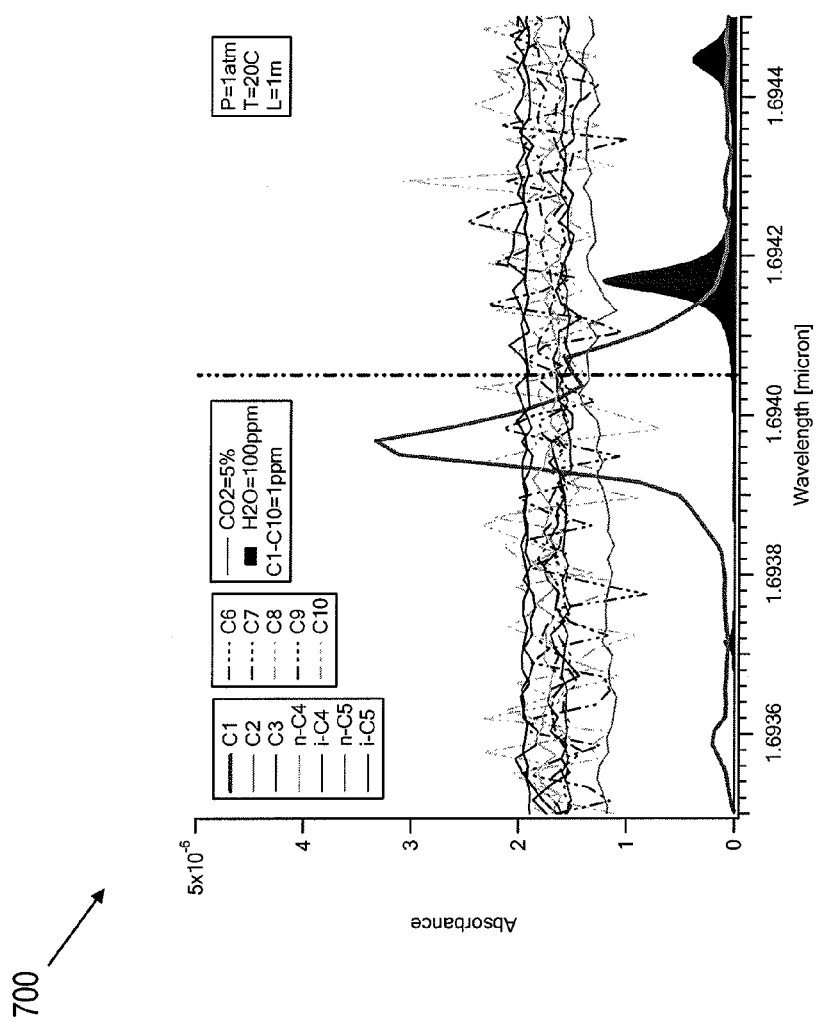
FIG. 7 is a graph showing absorption spectra for hydrocarbons having between one and ten carbons at wavelengths near 1.694 µm.

The lines at 2270.31 nm and 2261.15 nm listed in Table 2 have the best standard deviation among the hydrocarbons as shown in the right column. However, both of these lines also occur on the edge of large $CH_4$ spectral features as illustrated in FIG. 4 and FIG. 5. Interference from methane absorption lines can lead to the measurement uncertainty for the total HC measurement being quite large due to the steep slope of the methane spectra at these wavelengths, especially in the natural gas in which where methane is the dominant component (generally >80%). Under these circumstances, other candidate wavelengths listed in Table 2 and shown in FIGS. 4-7 may be more amenable to higher accuracy determination of the total HC concentration.

In an alternative implementation, the $CH_4$ concentration in a gas stream can be measured independently using TDLAS, and the total percentage of higher molecular weight hydrocarbons can be determined using absorption measurements at another wavelength at which these larger hydrocarbon molecules have similar levels of absorption and are not subject to $CH_4$ interference. This approach can be effective at least because $CH_4$ spectra tend to be more structured than the higher molecular weight hydrocarbons, which have a greater number of inter-atomic bonds and associated vibrational and rotational degrees of freedom that can be stimulated by absorption of an infrared photon. The lower structure of the higher molecular weight hydrocarbons facilitates their differentiation from methane absorption lines. Table 3 lists wavelengths where $C_2$-$C_{10}$ have similar levels of absorbance to methane and that satisfy the following criteria: the total absorbance for a total mole fraction of 10% of all 11 HC's and an absorption cell of at least 10 cm path length is within a range of approximately 0.01-10.0, the standard deviation of these 11 absorbances at a given wavelength is less than approximately 20%, and the absorbance for a 90% mole fraction of $CH_4$ is less than approximately 1% of the total absorbance for a 10% mole fraction of all $C_2$-$C_{10}$ absorptions at the same path length.

As listed in Table 3, the useful wavelengths tend to be located in the mid-infrared region where the use of quantum cascade lasers may be advantageous due to the current lack of semiconductor diode lasers available at these wavelengths.

TABLE 3

Candidate Wavelengths for Total HC Measurement Without $CH_4$

| Frequency (cm$^{-1}$) | Wavelength (nm) | C2-C10 Absorbance | STD (%) | Absorbance Ratio - C1/[C2-C10] (%) |
|---|---|---|---|---|
| 3244.70 | 3081.95 | 0.019 | 18.5 | 1.0 |
| 3244.40 | 3082.23 | 0.019 | 17.8 | 0.9 |
| 3244.34 | 3082.29 | 0.019 | 17.7 | 0.7 |
| 3244.28 | 3082.35 | 0.019 | 18.1 | 0.6 |
| 3244.22 | 3082.40 | 0.019 | 16.3 | 0.6 |
| 3244.16 | 3082.46 | 0.019 | 16.8 | 0.7 |
| 3244.10 | 3082.52 | 0.019 | 16.8 | 0.8 |
| 3242.78 | 3083.78 | 0.021 | 16.1 | 0.9 |
| 3242.72 | 3083.84 | 0.020 | 15.1 | 0.9 |
| 3242.65 | 3083.89 | 0.020 | 15.7 | 1.0 |
| 3241.99 | 3084.52 | 0.020 | 18.1 | 1.0 |
| 3241.93 | 3084.58 | 0.020 | 17.3 | 0.8 |
| 3241.87 | 3084.64 | 0.020 | 17.4 | 0.7 |
| 3241.81 | 3084.70 | 0.021 | 17.9 | 0.7 |
| 3241.75 | 3084.75 | 0.021 | 16.9 | 0.7 |
| 3241.69 | 3084.81 | 0.021 | 16.4 | 0.8 |
| 3241.63 | 3084.87 | 0.021 | 15.7 | 0.9 |
| 3241.57 | 3084.93 | 0.021 | 15.9 | 0.9 |
| 3241.39 | 3085.10 | 0.021 | 17.4 | 1.0 |
| 3241.33 | 3085.15 | 0.021 | 18.1 | 0.9 |
| 3241.27 | 3085.21 | 0.021 | 18.7 | 0.9 |
| 3239.22 | 3087.16 | 0.022 | 18.2 | 1.0 |
| 3239.16 | 3087.22 | 0.023 | 17.0 | 0.9 |
| 3239.10 | 3087.28 | 0.023 | 17.7 | 0.9 |
| 3239.04 | 3087.34 | 0.023 | 17.7 | 0.9 |
| 1488.53 | 6718.02 | 0.398 | 19.5 | 0.6 |
| 1488.35 | 6718.83 | 0.395 | 19.2 | 0.4 |
| 1485.58 | 6731.37 | 0.492 | 14.1 | 0.8 |
| 1485.52 | 6731.64 | 0.498 | 13.5 | 0.7 |
| 1485.46 | 6731.92 | 0.488 | 15.9 | 0.8 |

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices. (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The computing system may include clients and servers. A client and server are generally remote from each other and typically interact through a communication network. The relationship of client and server arises by virtue of computer programs running on the respective computers and having a client-server relationship to each other.

The subject matter described herein may be embodied in systems, apparatus, methods, and/or articles depending on the desired configuration. Although a few variations have been described in detail above, other modifications, additions, and implementations are possible are within the scope and spirit of the disclosed subject matter. Features implementing functions may also be physically located at various positions, including being distributed such that portions of functions are implemented at different physical locations. Further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results.

What is claimed:

1. An apparatus comprising:
a first sensor producing a first data signal characterizing a carbon dioxide concentration in the gas stream, the first sensor comprising a tunable diode laser absorption spectrometer comprising a laser light source that is scanned over a wavelength range that includes a selected absorption transition for carbon dioxide and a detector that detects an intensity of light reaching the detector after light from the laser light source passes through the gas stream, the first data signal comprising the intensity as a function of wavelength; and
a master processor that performs operations comprising:
receiving the first data signal and measurements of pressure and temperature in the gas stream,
fitting at least one region in the wavelength range outside of the selected absorption transition to a function to obtain a zero-absorption baseline,
determining the carbon dioxide concentration based on a line strength at the selected absorption transition corrected by the zero-absorption baseline,
inferring a total hydrocarbon concentration in the gas stream based on a database of characteristic natural gas concentrations, and
implementing an algorithm that determines an energy content of the gas stream using as inputs at least the measurements of temperature and pressure, the carbon dioxide concentration, and the inferred total hydrocarbon concentration the algorithm.

2. An apparatus as in claim 1, wherein the operations performed by the master processor further comprise calculating a total nitrogen and inert species concentration in the gas stream as a remainder when the calculated carbon dioxide concentration and the inferred total hydrocarbon concentration are subtracted from 100%, and wherein the calculated total nitrogen and inert species concentration is used as an additional input to the algorithm.

3. An apparatus as in claim 1, wherein the selected absorption transition for carbon dioxide is between approximately 2003 and 2004 nm.

4. An apparatus as in claim 1, wherein the wavelength range is between approximately 1300 nm and 2100 nm.

5. An apparatus as in claim 1, wherein the function is a low order polynomial.

6. An apparatus as in claim 1, wherein the detector comprises at least one of an indium gallium arsenide (InGaAs) photodiode, an indium arsenide photodiode, an indium antimonide detector, an indium arsenide (InAs) photodetector, a silicon (Si) photodetector, a germanium (Ge) photodiode, a mercury-cadmium-telluride (MCT) detector, and a lead-sulfide (PbS) detector.

7. An apparatus as in claim 1, further comprising one or more connections configured to attach to a fitting on a gas pipeline to divert the sample gas stream from the gas pipeline to the first sensor.

8. A computer-implemented method comprising:
receiving a first data signal characterizing a carbon dioxide concentration in a gas stream, the first data signal being generated by a first sensor comprising a tunable diode laser absorption spectrometer comprising a laser light source that is scanned over a wavelength range that includes a selected absorption transition for carbon dioxide and a detector that detects an intensity of light reaching the detector after light from the laser light source passes through the gas stream, the first data signal comprising the intensity as a function of wavelength;
fitting at least one region in the wavelength range outside of the selected absorption transition to a function to obtain a zero-absorption baseline
determining the carbon dioxide concentration based on a line strength at the selected absorption transition corrected by the zero-absorption baseline;
receiving measurements of pressure and temperature in the gas stream;
inferring a total hydrocarbon concentration in the gas stream based on a database of characteristic natural gas concentrations, and
implementing an algorithm that determines an energy content of the gas stream using as inputs at least the measurements of temperature and pressure, the carbon dioxide concentration, and the inferred total hydrocarbon concentration.

9. A method as in claim 8, further comprising calculating a total nitrogen and inert species concentration in the gas stream as a remainder when the calculated carbon dioxide concentration and the inferred total hydrocarbon concentration are subtracted from 100%, and wherein the calculated total nitrogen and inert species concentration is used as an additional input to the algorithm.

10. A method as in claim 8, wherein the selected absorption transition for carbon dioxide is between approximately 2003 and 2004 nm.

11. A method as in claim 8, wherein the wavelength range is between approximately 1300 nm and 2100 nm.

12. A method as in claim 8, wherein the function is a low order polynomial.

13. A method as in claim 8, wherein the detector comprises at least one of an indium gallium arsenide (InGaAs) photodiode, an indium arsenide photodiode, an indium antimonide detector, an indium arsenide (InAs) photodetector, a silicon (Si) photodetector, a germanium (Ge) photodiode, a mercury-cadmium-telluride (MCT) detector, and a lead-sulfide (PbS) detector.

14. A computer program product comprising a non-transitory machine-readable medium storing instructions that, when executed by at least one programmable processor, cause the at least one programmable processor to perform operations comprising:

receiving a first data signal characterizing a carbon dioxide concentration in a gas stream, the first data signal being generated by a first sensor comprising a tunable diode laser absorption spectrometer comprising a laser light source that is scanned over a wavelength range that includes a selected absorption transition for carbon dioxide and a detector that detects an intensity of light reaching the detector after light from the laser light source passes through the gas stream, the first data signal comprising the intensity as a function of wavelength;

fitting at least one region in the wavelength range outside of the selected absorption transition to a function to obtain a zero-absorption baseline determining the carbon dioxide concentration based on a line strength at the selected absorption transition corrected by the zero-absorption baseline;

receiving measurements of pressure and temperature in the gas stream;

inferring a total hydrocarbon concentration in the gas stream based on a database of characteristic natural gas concentrations, and implementing an algorithm that determines an energy content of the gas stream using as inputs at least the measurements of temperature and pressure, the carbon dioxide concentration, and the inferred total hydrocarbon concentration.

15. A computer program product as in claim 14, wherein the operations further comprise calculating a total nitrogen and inert species concentration in the gas stream as a remainder when the calculated carbon dioxide concentration and the inferred total hydrocarbon concentration are subtracted from 100%, and wherein the calculated total nitrogen and inert species concentration is used as an additional input to the algorithm.

16. A computer program product as in claim 14, wherein the selected absorption transition for carbon dioxide is between approximately 2003 and 2004 nm.

17. A computer program product as in claim 14, wherein the wavelength range is between approximately 1300 nm and 2100 nm.

18. A computer program product as in claim 14, wherein the function is a low order polynomial.

* * * * *